United States Patent [19]

Anderson

[11] Plant 4,095

[45] Aug. 30, 1977

[54] NECTARINE TREE

[75] Inventor: Frederic W. Anderson, Merced, Calif.

[73] Assignee: Reedley Nursery, Inc., Reedley, Calif.

[21] Appl. No.: 719,051

[22] Filed: Aug. 30, 1976

[51] Int. Cl.[2] ..... A01H 5/03

[52] U.S. Cl. ..... Plt./41

[58] Field of Search ..... Plt./41

*Primary Examiner*—Robert E. Bagwill

*Attorney, Agent, or Firm*—Roger B. Webster

[57] ABSTRACT

A nectarine tree which is large, vigorous, upright to spreading, foliated with large to medium size, lanceolate, acutely pointed leaves having a glandular, crenate margin, and a regular and very productive bearer of large, uniform, symmetrical, globose to oblong, freestone fruit having yellow skin substantially overspread with red, yellow flesh, and a stone with a sweet kernel.

1 Drawing Figure

1

BACKGROUND OF THE VARIETY

Over a substantial number of years I have engaged in an extensive and continuing plant breeding program at my experimental nursery and orchard located near Le Grand, Merced County, Calif.; one purpose of such program being to provide improved varieties of fruit trees. The present variety of nectarine tree resulted from my endeavors in the conduct of such plant breeding program.

ORIGIN OF THE VARIETY

The present variety of nectarine tree was originated by me, in my experimental nursery and orchard located as aforesaid, as an $F_1$ cross of the Red Diamond nectarine (U.S. Plant Pat. No. 3,165) as the seed parent and the Early Sun Grand nectarine (U.S. Plant Pat. No. 1,420) as the pollen parent.

ASEXUAL REPRODUCTION OF THE VARIETY

Subsequent to origination and selection by me of the present variety of nectarine tree, in the manner above described, I asexually reproduced it by top-working on mature trees in my said experimental orchard, and — in maturity — such reproductions ran true to the original tree in all respects.

SUMMARY OF THE VARIETY

The herein claimed new and distinct variety of nectarine tree is large, vigorous, upright to spreading, foliated with large to medium size, lanceolate, acutely pointed leaves having a glandular, crenate margin, and a regular and very productive bearer of large, uniform, symmetrical, globose to oblong, freestone fruit having yellow skin substantially overspread with red, yellow flesh, and a stone with a sweet kernel; the fruit being quite similar to that of the Red Diamond nectarine including comparable shipping quality and hence is adapted for long distance marketing, but ripens about two weeks later whereby the marketing season for such type of fruit is desirably extended.

BRIEF DESCRIPTION OF THE DRAWING

The drawing is an illustration, by photographic reproduction in color, of leaves and fruit of the variety; one of the fruit being cut into halves to expose the flesh, with the stone remaining in one such half.

2

DESCRIPTION OF THE VARIETY

The botanical details of this new and distinct variety of nectarine tree — with color definitions (except those in common color terms) referenced to Maerz and Paul Dictionary of Color — are as follows:

Tree:
- *Size.*—Large.
- *Vigor.*—Vigorous.
- *Growth.*—Upright to spreading.
- *Production.*—Very productive.
- *Bearing.*—Regular bearer.

Trunk:
- *Size.*—Medium.
- *Texture.*—Medium.

Branches:
- *Size.*—Medium.

Leaves:
- *Size.*—Large to medium. Average length — 6". Average width — 1¼".
- *Form.*—Lanceolate. Acutely pointed.
- *Margin.*—Glandular. Crenate.
- *Petiole.*—Medium length — average 7/16". Medium thickness.
- *Glands.*—Number and position — 2 on petiole and 1 to 4 on blade. Alternate. Medium size. Reniform.
- *Color.*—Top Side — Medium green (23-L-9). Under side — Lighter green (22-K-7).

Flowers:
- *Blooming Period.*—Medium, as compared with other varieties.
- *Size.*—Medium.

Fruit:
- *Maturity when described.*—Eating ripe.
- *Date of first picking.*—July 5, 1976.
- *Date of last picking.*—July 24, 1976.
- *Size.*—Large. Uniform. Average diameter axially — 2½". Average transversely in suture plane — 2⅜".
- *Form.*—Uniform. Symmetrical. Globose to oblong.
- *Suture*—Distinct. Extends from base to apex, with marked depression beyond pistil point.
- *Base.*—Rounded.
- *Apex.*—Short. Depressed.

Skin:

*Thickness.*—Medium.

*Texture.*—Tough.

*Tendency to crack.*—None noted.

*Down.*—Wanting.

*Color.*—Yellow (10-L-6) substantially overspread with red (5-L-6) shading darker to 7-L-6, with some yellow flecking.

Flesh:

*Texture.*—Firm. Crisp. Meaty.

*Ripens.*—Evenly.

*Flavor.*—Subacid.

*Eating quality.*—Good to best.

*Color.*—Yellow (10-K-7) with flecks of red in flesh.

*Surface of pit cavity.*—Red (5-K-4) with red streaked slightly into flesh.

Stone:

*Type.*—Free. Parts from flesh smoothly.

*Size.*—Medium. Average length — 1 5/16". Average breadth — $\frac{7}{8}$". Average thickness — $\frac{3}{4}$".

*Form.*—Oval.

*Sides.*—Equal.

*Kernel.*—Sweet.

*Tendency to split.*—Slight.

*Color.*—Brown (8-H-11).

Use: Market — local. Dessert. Long distance shipping.

Keeping quality: Good.

Resistance to insects and diseases: No unusual susceptibilities noted.

Shipping quality: Very good.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, which is large, vigorous, upright to spreading, foliated with large to medium size, lanceolate, acutely pointed leaves having a glandular, crenate margin, and a regular and very productive bearer of large, uniform, symmetrical, globose to oblong, freestone fruit having yellow skin substantially overspread with red, yellow flesh, and a stone with a sweet kernel; the fruit being quite similar to that of the Red Diamond nectarine, but ripens about two weeks later.

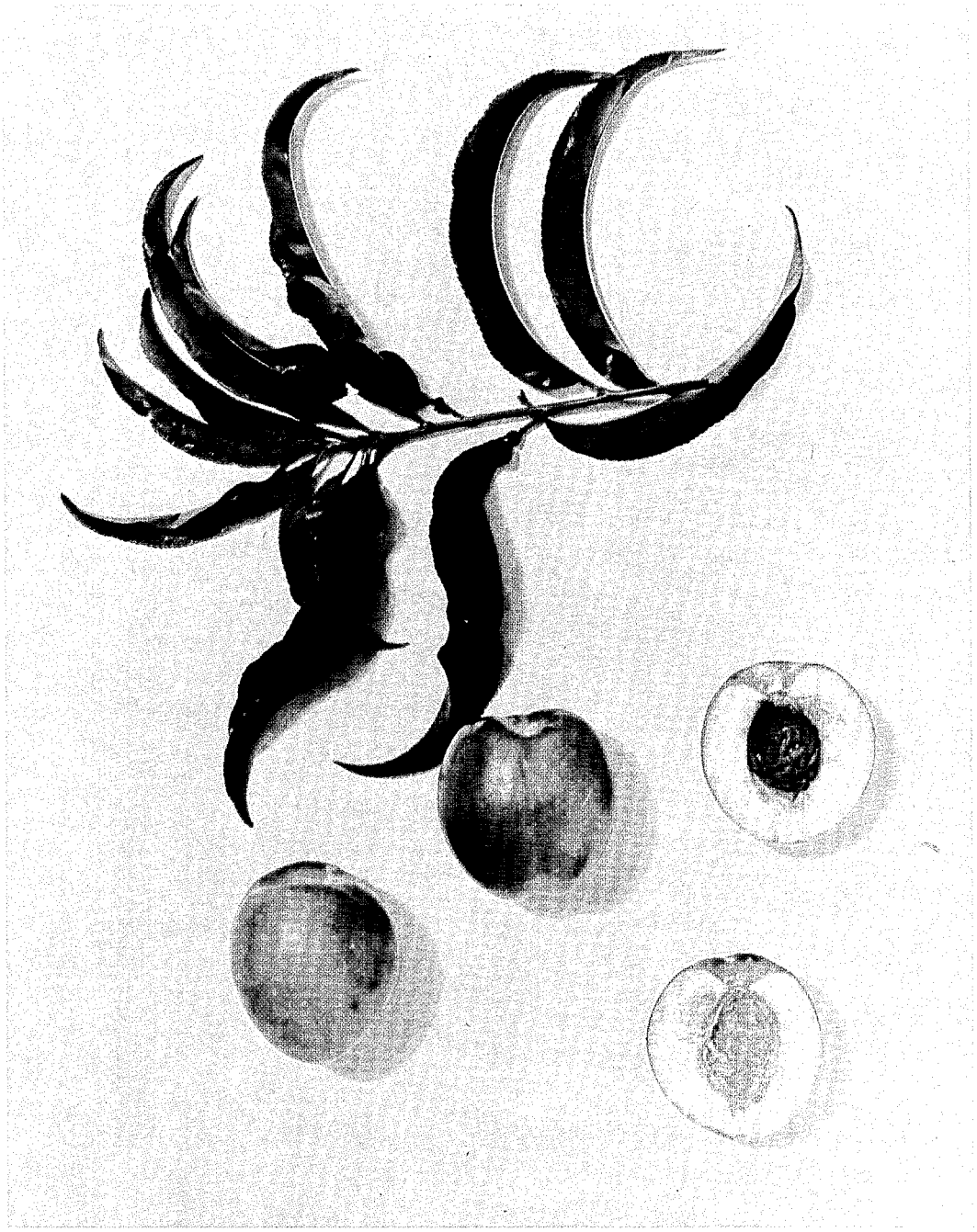

* * * * *